United States Patent
Ellingboe et al.

(10) Patent No.: US 6,802,855 B2
(45) Date of Patent: Oct. 12, 2004

(54) PATIENT TEMPERATURE CONTROL SYSTEM CONNECTOR APPARATUS

(75) Inventors: Bruce Ellingboe, Littleton, CO (US); Michael R. Hoglund, Mead, CO (US); Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 0 days.

(21) Appl. No.: 10/215,302

(22) Filed: Aug. 8, 2002

(65) Prior Publication Data

US 2004/0030373 A1 Feb. 12, 2004

(51) Int. Cl.[7] .................................................. A61F 7/00
(52) U.S. Cl. ...................................... 607/104; 607/108
(58) Field of Search ........................ 607/96, 104, 105, 607/108–112; 137/597, 266, 884; 5/713; 285/148.14

(56) References Cited

U.S. PATENT DOCUMENTS

| | | | |
|---|---|---|---|
| 3,894,213 A | 7/1975 | Agarwala | 219/297 |
| 4,118,946 A | 10/1978 | Tubin | 62/514 R |
| 4,508,123 A | 4/1985 | Wyatt et al. | 128/692 |
| 4,691,762 A * | 9/1987 | Elkins et al. | 165/46 |
| 4,951,665 A | 8/1990 | Schneider | 128/400 |
| 4,982,736 A | 1/1991 | Schneider | 128/400 |
| 5,097,829 A | 3/1992 | Quisenberry | 128/400 |
| 5,344,436 A | 9/1994 | Fontenot et al. | 607/104 |
| 5,411,541 A | 5/1995 | Bell et al. | 607/104 |
| 5,456,701 A | 10/1995 | Stout | 607/104 |
| D364,680 S | 11/1995 | Dye | D24/129 |
| 5,470,353 A | 11/1995 | Jensen | 607/104 |
| 5,507,792 A | 4/1996 | Mason et al. | 607/104 |
| 5,643,191 A | 7/1997 | Buckberg et al. | 604/4 |
| 5,895,418 A | 4/1999 | Saringer | 607/104 |
| 5,944,362 A * | 8/1999 | Harle | 285/148.14 |
| 6,197,045 B1 | 3/2001 | Carson | 607/104 |
| 6,212,718 B1 * | 4/2001 | Stolpmann et al. | 5/713 |
| 6,238,427 B1 | 5/2001 | Matta | 607/104 |
| 6,394,138 B1 * | 5/2002 | Vu et al. | 137/884 |
| 6,425,414 B2 * | 7/2002 | Jorgensen et al. | 137/597 |
| 6,547,284 B2 * | 4/2003 | Rose et al. | 285/1 |

* cited by examiner

Primary Examiner—Roy D. Gibson
(74) Attorney, Agent, or Firm—Marsh Fischmann & Breyfogle LLP

(57) ABSTRACT

A connector apparatus employable in a patient temperature control system includes a connection end which is employable for connecting to at least one other connector in the system. Includable in the connection end is an orientation device configured to align the connectors and provide for interconnection only at a predetermined orientation. The connector may be configured as either a male or female style connector and include one or more engagement devices or surfaces for engaging with another connector.

40 Claims, 18 Drawing Sheets

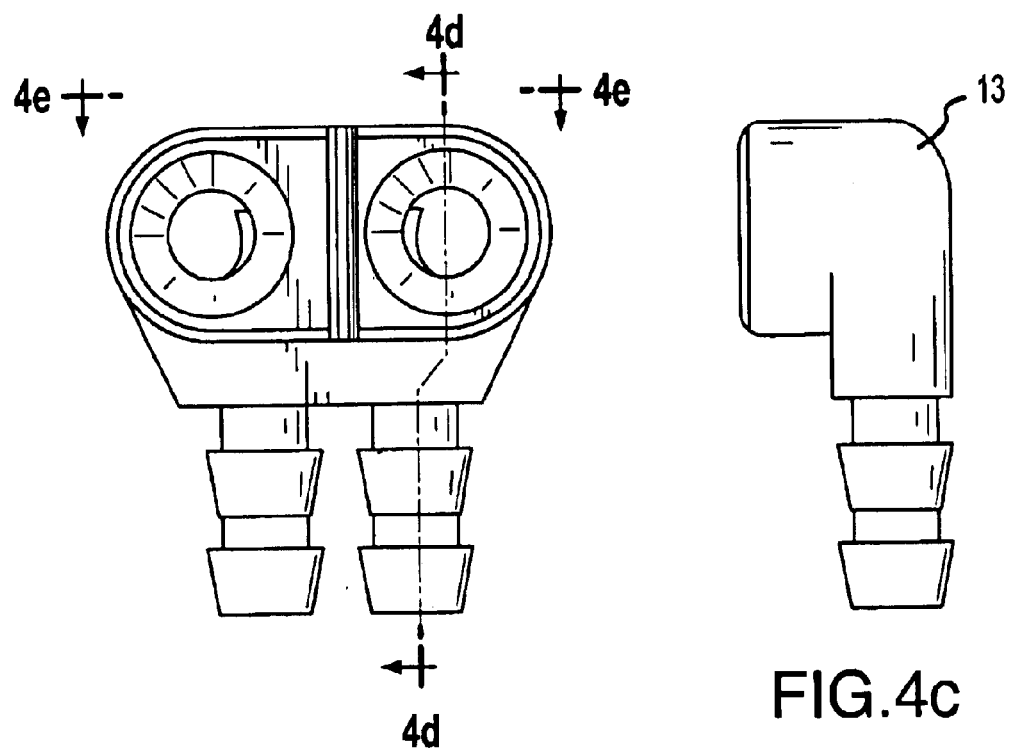
FIG.4b
FIG.4c
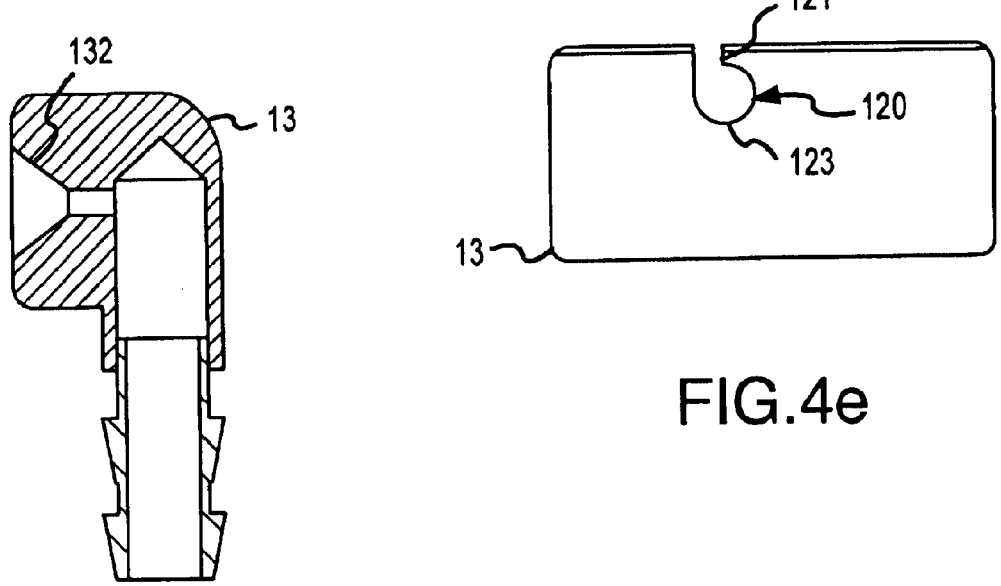
FIG.4d
FIG.4e

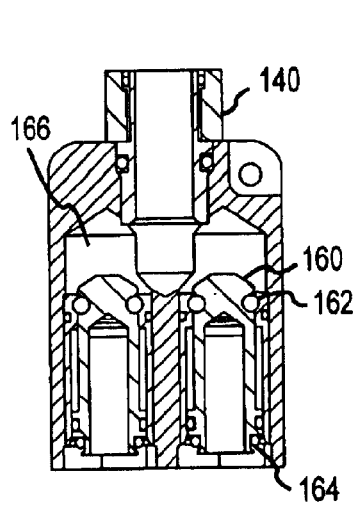
FIG.9f
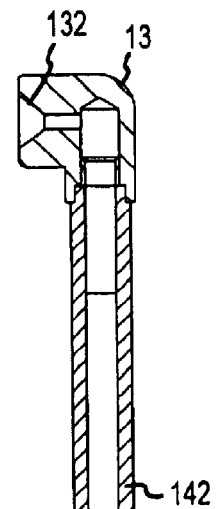
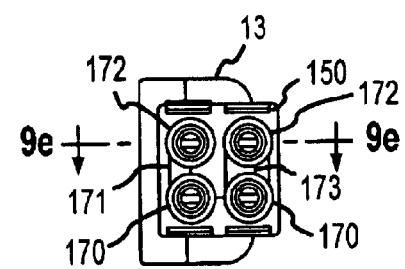
FIG.9e
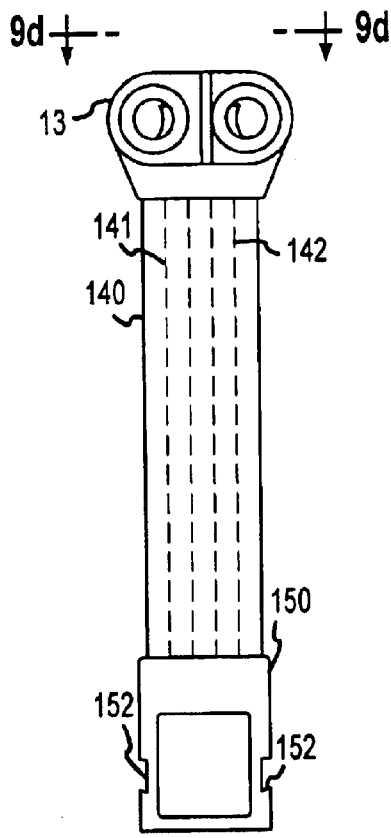
FIG.9b
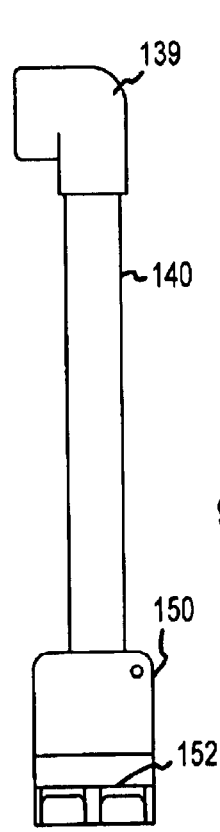
FIG.9c
FIG.9d

PATIENT TEMPERATURE CONTROL SYSTEM CONNECTOR APPARATUS

FIELD OF THE INVENTION

The invention described herein relates to systems and methods for use in patient temperature control, and more specifically to devices employable for interconnecting a temperature control device such as a heating/cooling pad to a medical fluid processing apparatus.

BACKGROUND OF THE INVENTION

The use of contact pad system for selectively cooling and/or heating bodily tissue is known. In such systems a fluid, (e.g. water or air), is circulated through one or more pads to affect surface to surface thermal energy exchange with a patient. One highly effective contact pad and related system is disclosed in U.S. Pat. No. 6,197,045, hereby incorporated by reference in its entirety. As noted in U.S. Pat. No. 6,197,045, the ability to establish and maintain intimate pad to patient contact is often key importance to fully realizing medical efficacies with contact pad systems.

Temperature management or thermal regulation can be viewed in two different ways. The first aspect of temperature management includes treating at normal body temperature (i.e. cooling the body for elevated temperatures or warming the body for lower temperature). The second aspect of thermal regulation is an evolving treatment that employs techniques that physically control a patient's temperature to provide a physiological benefit, such as cooling a stroke patient to gain some degree of neuro protection.

In view of the foregoing, it may be appreciated that recognized medical applications for contact pad systems are ever increasing. By way of example, cooling pad systems may be utilized in early therapy to reduce neurological damage incurred by stroke and head trauma patients. Additional applications include selected patient heating/cooling during surgical procedure such as cardio pulmonary bypass operation.

As these and other medical applications have evolved, the present inventors have recognized the desirability of enhancing the flexibility and portability of thermal exchange fluid systems. More particularly, while heating/cooling contact pads systems have proven effective for many applications, the present inventors have recognized that additional performance and potential applications can be realized via implementation of further improved hose and connector device assemblies.

SUMMARY OF THE INVENTION

Disclosed herein is a connector for use in a patient temperature control system wherein the patient temperature system includes a medical fluid processing apparatus employable for circulating medical fluid. The connector may include a body portion configured with a plurality of fluid channels formed therethrough. The body portion may be further configured to be one of interconnected and interconnectable with at least one medical fluid processing apparatus and a patient temperature control pad through which medical fluid may be circulated. Further configured in the body portion of the connector may be an interconnection end configured to interconnect with at least one other connector employable in the patient temperature control system. Includable in the interconnection end may be at least one orientation device configured to provide for the interconnection of the connector and the at least one other connector at an orientation which provides for circulation of the medical fluid through the system in a predetermined direction.

In one configuration of the invention the connector may be configured as a female connector. The female connector may include a body portion with a plurality of fluid channels formed therethrough. Incorporated in the body portion may be a receiving end which includes openings to the fluid channels, where the receiving end is further configured to receive and fluidly seal with a male connector insertable therein. Further includable in the receiving end may be a rotatable engagement device which extends through at least a portion of the receiving end, where the rotatable engagement device is configured to pass within a portion of a male connector and upon rotation of the rotatable engagement device mechanically engage the male connector.

In one configuration of the invention, the female connector may be incorporated as part of the housing of the medical temperature control system and be in communication with one or more components included therein. Further, the receiving end may include a wall structure which surrounds a cavity within which the openings to the fluid channels are locatable. The rotational engagement device may include at least one shaft like member, portions of which extend through the walls of the wall structure. Locatable outside the wall structure may be a manipulation arm configured for rotating the shaft like member within the cavity to one or more desired rotational orientations. In yet another configuration of the invention, the shaft like member may include a cross-sectional shape of a semi-circle, wherein the profile of the shaft like member is substantially narrow at a first relative orientation and substantially wide at the second relative orientation.

The connector may be further configured as a male machine connector which may comprise a body portion through which a plurality of flow channels are formed. Incorporated in the body portion may be an insertion end configured to include openings to the fluid channels and be insertable within a portion of a female machine connector so as to establish a plurality of sealed fluid path through the male and female machine connectors. Included in the male connector may be at least one engagement portion which is configured to receive an engagement device incorporated in a female machine connector where manipulation of the engagement device provides for the mechanical connection of the male and female machine connectors.

In one configuration of the male machine connector, the engagement portion may be configured to receive a rotational engagement device wherein once the rotational engagement device is within the engagement portion, rotation of said device provides for the mechanical engagement of the connectors. In particular, the engagement portion may comprise a slot like structure which allows a portion of the rotatable engagement device to pass within the slot at a first rotational orientation and then to engage and hold the male machine connector at a second rotational orientation. This engagement portion may be positioned on the body of the male machine connector such that the male and female machine connectors are only connectable at a pre-determined relative orientation.

In yet another configuration of the male machine connector, the body portion may be further connectable to a one-piece hose section with a plurality of channels formed therethrough. Further connectable to the one piece hose section maybe an intermediate connector further configured to connect to other connectors employable within the System. The intermediate connector may comprise an intermediate female connector device configured to interconnect with one or more assemblies which include a male intermediate connector. The hose assemblies may be one of interconnected or interconnectable to a patient temperature control pad.

The intermediate connector may be further configured as a female intermediate connector which includes a body portion with a plurality of fluid channels formed therethrough wherein the body portion includes one or more receiving ends. The one or more receiving ends are specially configured to connect and fluidly seal with at least one male intermediate connector so as to provide a plurality of fluidly sealed flow paths therethrough. The intermediate female connector may be further configured to include at least one orientation device which provides for the interconnection of the intermediate female connector with a male intermediate connector at a predetermined relative orientation. In one configuration of the invention, the orientation device may be a member which extends into the receiving end of the intermediate female connector so as to incorporate a non-symmetrical feature.

Further incorporated into the body portion of the intermediate female connector may be an engagement surface configured to being engaged by an attachment device of a male intermediate connector insertable in the receiving end. The engagement surface may be configured as a ledge and/or interlocking lip structure. Also incorporated into the intermediate female connector may be at least one spring loaded valve device which is configured to provide fluid flow through the channels of the body portion upon insertion of a male connector and to dose the channel upon removal of said male intermediate connector. The valve device may include a movable plunger in contact with at least one compressible spring, wherein upon insertion of the male connector in the receiving end, the plunger is moved and the spring is compressed thereby opening the channel for fluid flow.

The plunger and spring combination may be further employable during interconnection of the male and female intermediate connectors so as to maintain the connection between the connectors. An engagement surface, in particular an interlocking lip on the male intermediate connector, may interlock with the engagement surface on female intermediate connector after insertion. In order to maintain the connection, the spring may exert an ejection forced on the male intermediate connector which maintains the connection between the interlocking lips. The body portion of the female intermediate connector may be further configured to include a plurality of the engagement surfaces, such that simultaneous manipulation of the engagement devices on the male connector is required in addition to an application of an insertion force in order to disengage the male intermediate connector from the female intermediate connector.

The connector may be further configured as an intermediate male connector which includes a body portion with a plurality of fluid channels formed therethrough. The body portion is further configured with an insertion end configured to be insertable in a female intermediate connector and to engage therewith. The male intermediate connector is further configured to be interconnected and/or interconnectable to at least one patient temperature control pad.

Further included as part of the insertion end may be at least one orientation device configured so that the male intermediate connector is insertable within the female intermediate connector at a predetermined relative orientation. In one configuration of the invention, the orientation device may be a non-symmetrical feature configured into the insertion end. More specifically, the orientation device comprises an alignment flange which extends between the fluid channels.

The male intermediate connector may be further configurable to include at least one engagement device positionable on an exterior surface of the body portion, said engagement device being manipulable to engage and disengage an engagement surface an a female intermediate connector when the insertion end is inserted in a receiving portion of the female intermediate connector. The engagement and disengagement may be through single handed manipulation.

In one configuration of the invention the engagement device may include at least one flex arm extending substantially perpendicular from the body portion, a latch arm positionable at the end of the flex arm away from the body, wherein the latch arm includes a depressible portion configured on a first end and an engagement portion configured on a second end opposite the first end. The flex arm is connectable to the latch arm in a manner such that application of a force to the first end rotates the second end and flex arm about the point of attachment of the fled arm and the body, and removal of the force returns the flex arm and latch arm to the original position.

The engagement portion of the latch arm may be configured with at least one interlocking lip, such that when the engagement portion engages a matching interlocking surface on the female intermediate connector and a force is applied to keep the interlocking lips together, the engaged structure resists lateral movement thus maintaining interconnection between connectors. In one configuration of the invention the male connector may include a plurality of the engagement devices. The engagement devices may be further configured such that simultaneous manipulation of the plurality of engagement devices is necessary in order to engage and/or disengage the connector. In particular, during disengagement of the connectors a continuous simultaneous may be applied (for example, with a thumb and finger on the same hand) until the engagement devices clear the engagement surfaces of the female intermediate connector during removal of the male intermediate connector.

BRIEF DESCRIPTION OF THE DRAWINGS

FIGS. 4a–e disclose views of the male machine connector.

FIGS. 9a–f disclose views of one configuration of the male connector assembly.

DETAILED DESCRIPTION

Figure 1:
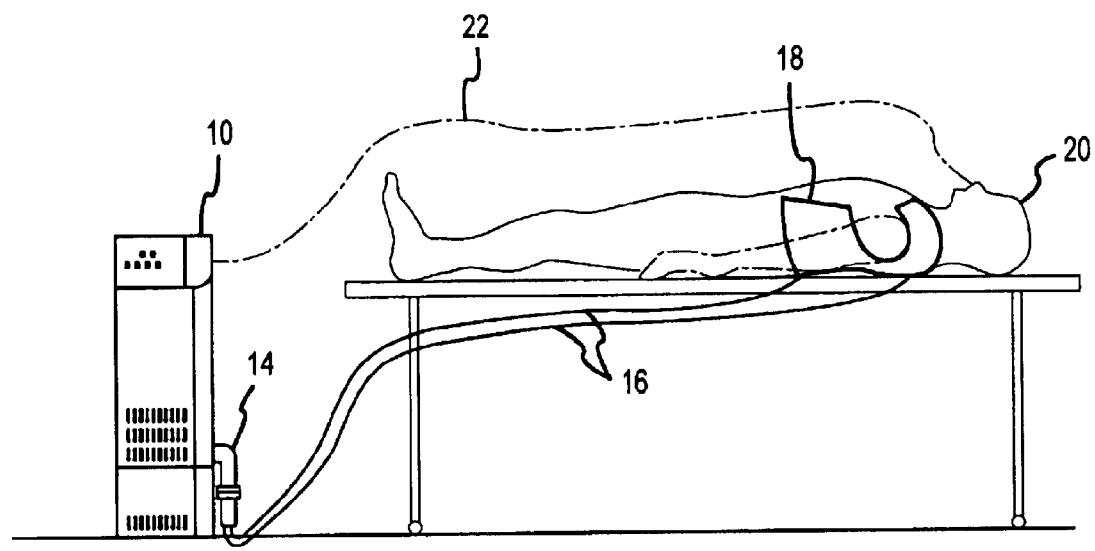
FIG. 1 is a view of a patient temperature control system with which the present invention may be employed.

Disclosed in FIG. 1 is an exemplary configuration of the temperature control system which is employable to provide heating/cooling of a patient 20. By way of example, pads 18 positionable on a patient 20 may be of the type described in U.S. Pat. No. 6,197,405. The system 10 is employable for circulating temperature control fluid through the pad 18. The system 10 may include a circulating pump for drawing fluid (e.g. water) through the pads, a circulating reservoir as well as one or more heat exchange devices for heating/cooling fluid circulating through the system. Also included may be a temperature sensor 22 employable for monitoring patient temperature.

Interconnecting the patient temperature control system 10 and the pads 18 is hose and is connector assembly 14. Included in the assembly 14 may be one or more individual connectors, as well as lengths of hose 16 which act as delivery and return lines for the fluid circulated between system 10 and pads 18.

Figure 2:
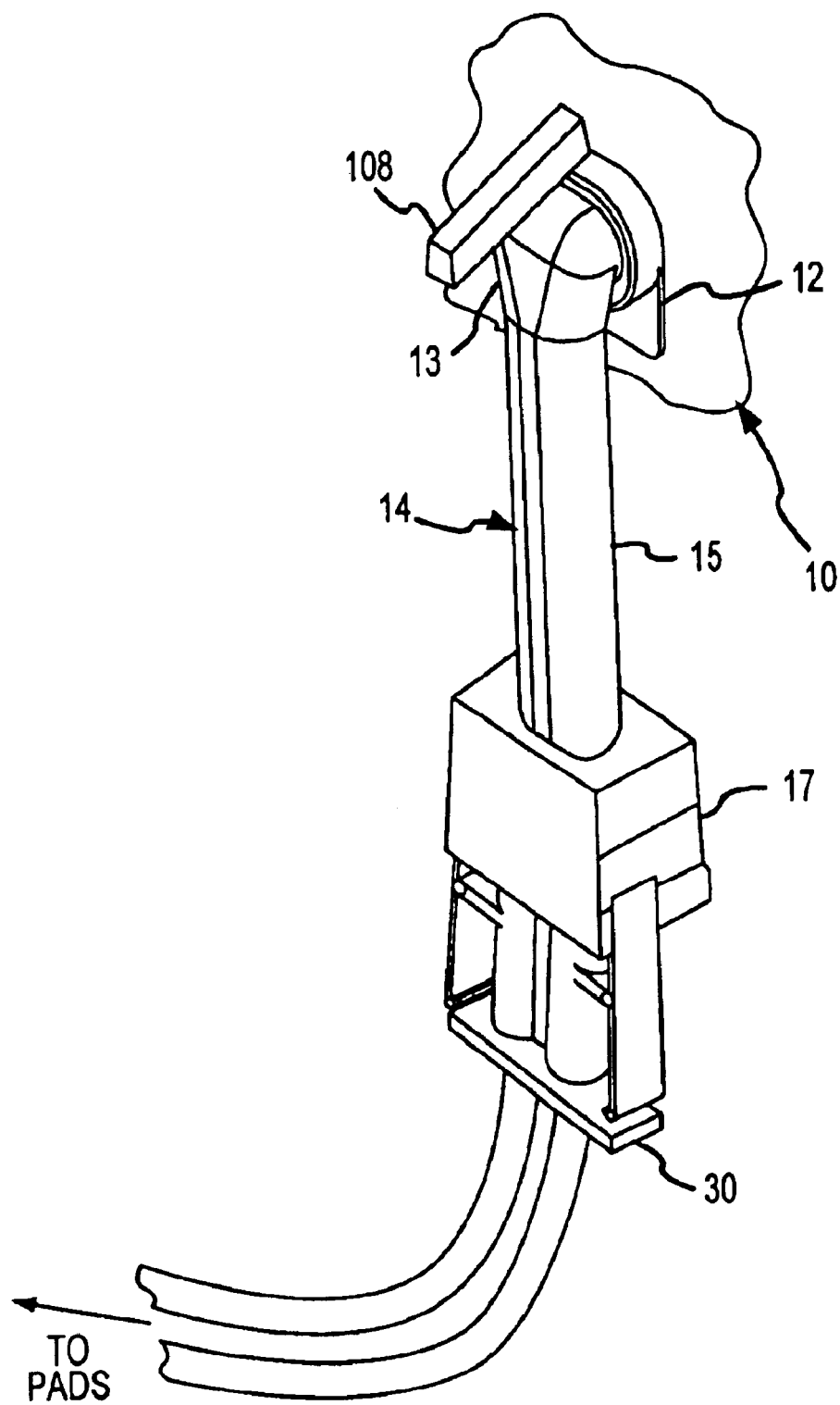
FIG. 2 is a view of one configuration of a hose and connector assembly.

Disclosed in FIG. 2 is a view of the hose and connector assembly 14 interconnected with system 10, specifically including the various connectors which may be employed in order to connect the patient temperature control system 10 to the patient temperature control pad(s). Shown in particular is female machine connector 12, which provides for the attachment of the hose assembly 14 to the control system 10. The female machine connector 12 may be incorporated into system 10 and be in fluid communication with the various reservoirs and heat exchange devices included therein. The female machine connector 12 may include at least one receiving end for receiving a male machine connector 13 portion of the hose and connector assembly 14. To facilitate the connection with the male machine connector 13, the female machine connector 12 may include a connection device 108 which is manipulable to establish a fluid tight connection. The details of female machine connector 12 will be discussed in greater detail below.

As noted, the hose assembly 14 includes a male machine connector 13 configured to be insertable within the female machine connector 12 and be engaged. The male machine connector 13 may be attached to one-piece hose apparatus 15 which is further in connection with female intermediate connector 50. As will be described in greater detail below, the female intermediate connector 50 may include one or more receiving ends configured to receive and engage any number of male intermediate connectors 30. The male intermediate connectors 30 are further connectable through hoses 16 to the patient temperature control pads. The connection to the patient temperature control pads may be through a single length of hose or through various lengths of hose interconnected using one or more male and female intermediate connector combinations.

Figure 3A:
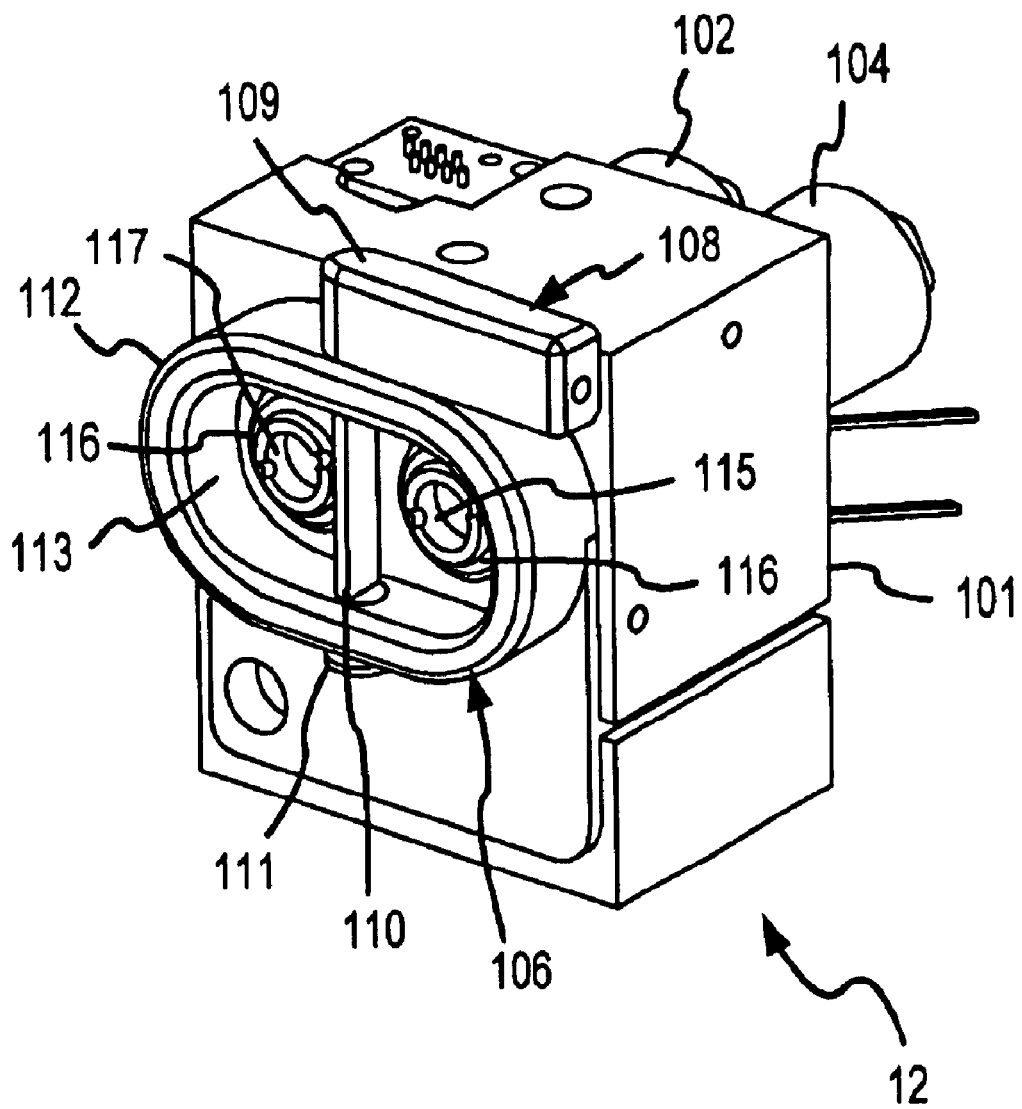
FIGS. 3a and b are views of the female machine connector.

With regards to the individual connectors, disclosed in FIGS. 3a and b are perspective and front views of female machine connector 12 which is mountable within the housing of temperature control system 10. Included in the female machine connector 12 is a receiving end 112 specially configured for receiving an insertion end 119 of a male machine connector 13. Included in particular is a wall structure 106 extending outward from the body 101 of connector 12. Within the wall structure is a cavity 113, which includes a cross section sized to fit with the insertion end 119 of a male machine connector 13 at a substantially close tolerance. Located within the receiving end 112 are openings for fluid channels 115 and 117 which extend above the floor of the cavity 113 and where each include at least one gasket device 116 for establishing a fluid tight seal. The fluid channels 115 and 117 pass through the female machine connector 12 and exit through channels 104 and 102 respectively. When installed in the temperature control system 10, these channels provide for the circulation of fluid to and from internal components of the system.

Extending within the cavity 113 is a rotational engagement device 108 which is configured to pass within an engagement portion of a male machine connector 13, and upon rotation mechanically engage said male machine connector 13. Included as part of the rotatable connection device is engagement shaft 110 which in the configuration of the invention shown in FIG. 3a is configured with a cross sectional shape of a semi-circle. The use of a semi-circle is exemplary, and any number other cross sectional shapes may be employable for this purpose.

Figure 3B:
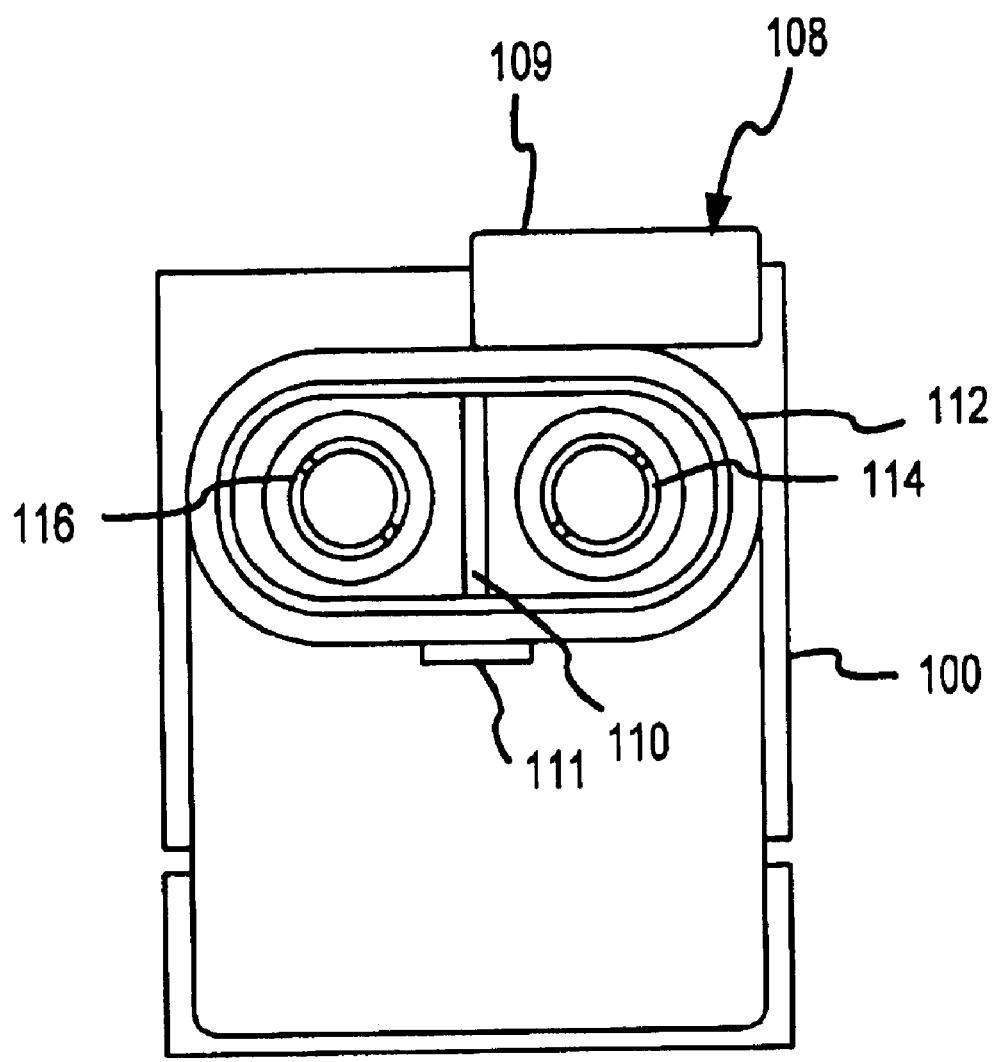

As can be better seen in the front view of FIG. 3b, the rotatable engagement device 108 further includes a retaining end 111 which passes through the wall portion of the cavity 113 and supports the engagement shaft at one end. At the opposite end of the engagement shaft 110 is the rotatable handle 108 which is rotatable to provide for the rotation of the engagement shaft 110. The handle portion 108 further includes retaining end portion which also passes within the wall structure 106. At either end of the shaft 110, the hole through the wall 106 provides a bearing surface for rotation of the shaft 110.

Figure 4A:
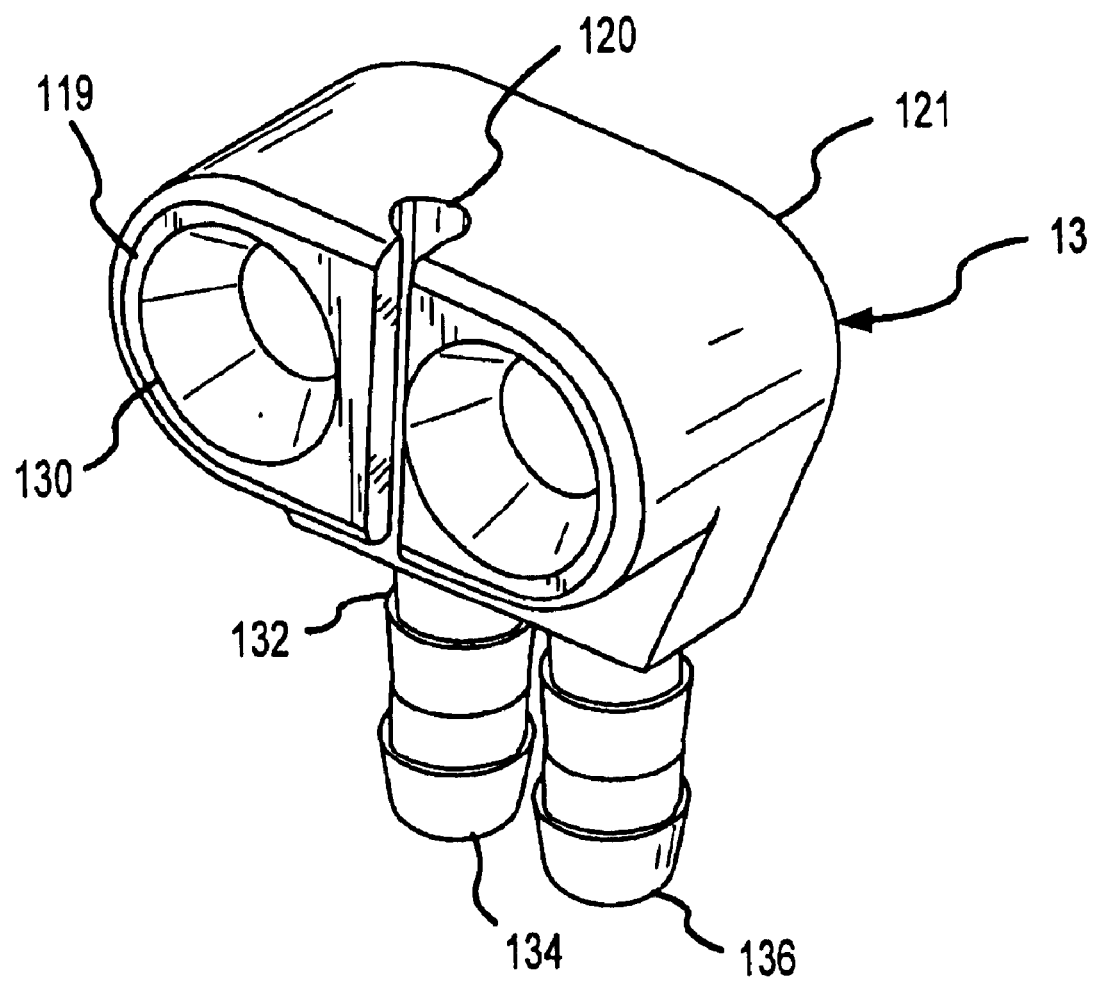

Disclosed in FIG. 4a is a geometric view of the male machine connector 13 employable to interconnect with female machine connector 12. The male machine connector 13 includes a body portion 121 through which two fluid channels 130 and 132 extend from insertion end 119 to attachment portions 134 and 136, respectively. The insertion end 119 disclosed herein is configured in an oval and/or racetrack type shape, although one skilled in the art would realize that any number of shapes is employable. Further, in the configuration shown in FIG. 4a, the fluid channels are configured to turn at substantially a 90° angle; however, one skilled in the art would realize that any number of configurations is possible.

As is seen in the cross section view of the connector in FIG. 4d, the interior surface fluid channels 130 and 132 are configured with a tapering cross section shape so that a fluid type seal may be created when the surfaces contact the fluid channels 115 and 117 in female machine connector 12. Attachment ends 134 and 136 may be configured to each attach to a hose for employable for circulating fluid to a remote device such as a temperature control pad. This configuration is especially applicable to connecting two lengths of hose between the system 10 and the patient temperature control pads without the use of any intermediate connectors. Alternatively, the attachment ends 134 and 136 may be replaced by a one-piece structure connectable to the body portion 121, where the one-piece structure includes a plurality of fluid channels passing therethrough. The one-piece structure may be further connectable to an intermediate connector. This configuration, including all its components, will be discussed in greater detail below.

Further incorporated in the male machine connector 13 is at least one engagement portion 120 specially configured to receive and mechanically engage with the engagement shaft 110 of the female machine connector 12. A view of the engagement portion 120 can be seen in the top view of the male machine connector 13 in FIG. 4e. In this configuration, it is seen that the engagement portion 120 includes a narrow, substantially rectangular slot 121 which opens up into a larger substantially circular area 123. This configuration allows the engagement shaft 110 to pass within the smaller slot 121 at a first rotational orientation and then once within the cylindrical area 123, rotate to a second rotational position whereby the relative width of the shaft 110 is greater than the slot 121. At this second orientation, shaft 110 contacts a portion of the interior surface of the circular area 123 such that the male and female machine connectors 13, 12 are mechanically engaged. The rectangular slot 121 may be further configured in the connector to act as an orientation device. In one configuration of the invention the slot is positioned closer to one channel through the connector than the other. This non-symmetry has the effect that the male and female machine connectors 13, 12 may only be connected one relative orientation thus ensuring that fluid through the system flows in the proper direction.

Figure 5A:
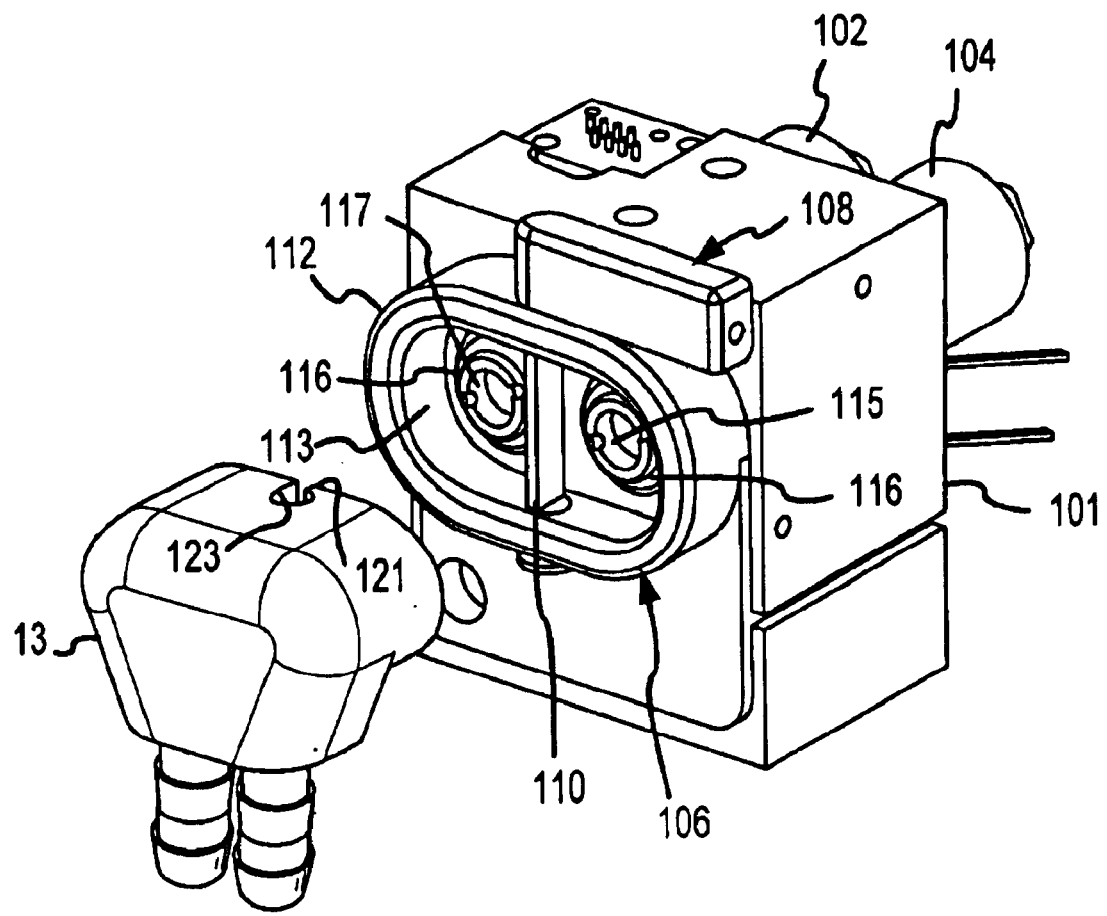
FIGS. 5a and b disclose geometric views of the male and female machine connectors in operation.
Figure 5B:
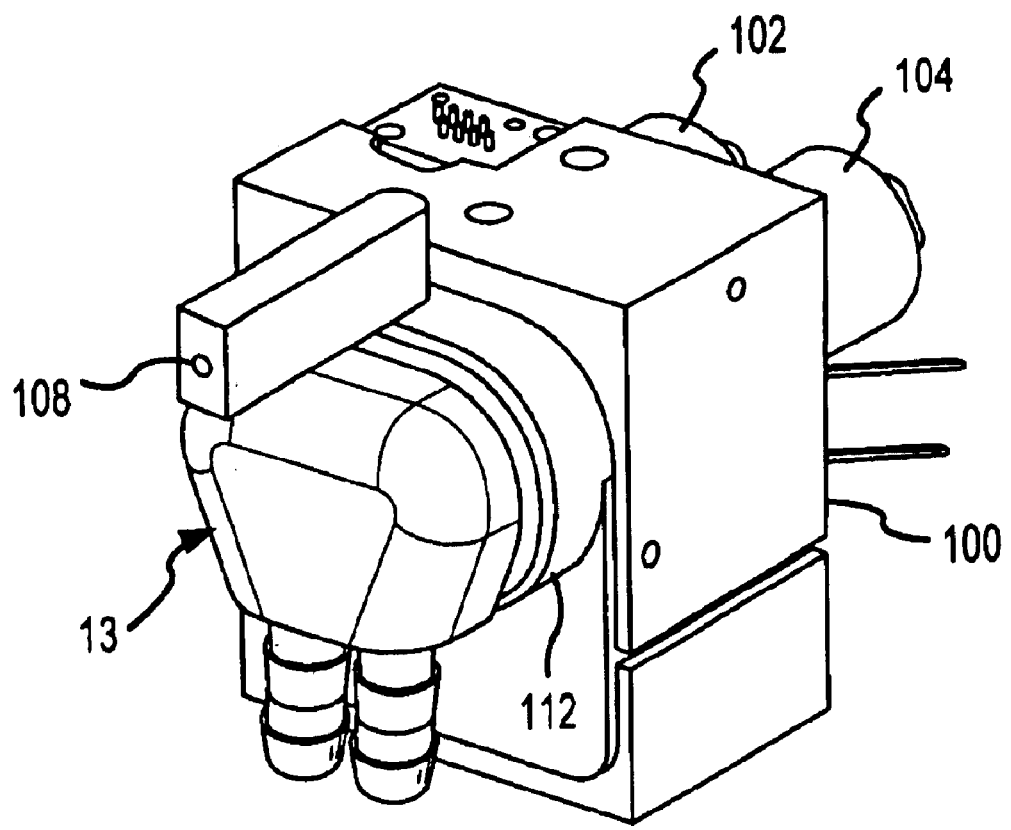

The views showing the engagement and disengagement of the male and female machine connectors 13, 12 are provided in FIGS. 5a and b. Seen in particular in FIG. 5a, prior to interconnection of these components, the male machine connector 13 is aligned with the receiving end 112 of the female machine connector 12. In particular, it is seen that the exterior of the male machine connector 13 is substantially the same shape as the receiving end 112 so that a substantially close tolerance fit may be achieved. Further, it is seen that the rotational connection device is in a first rotational position whereby the engagement shaft 110 is at its minimum cross section with regards to its position relative to engagement slot 121.

Once the components are aligned, the male machine connector 13 may be inserted in receiving end 112 in a manner such that the engagement shaft 110 passes within the slot 121. Once the internal channels of the male machine connector 13 head contact the protruding openings of the female machine connector 12 and the rotation shaft 110 passes within the cylindrical area 123, the handle of the rotational engagement device 108 may be rotated in a manner which is shown in FIG. 4b. This movement of the handle acts to rotate the engagement shaft 110 within the cylindrical portion 123 of the engagement slot 121 such that mechanical contact is created between the engagement shaft 123 and the interior surfaces of the cylindrical portion and a compressive force is applied between the male and female machine connectors 13, 12 such that a plurality of fluidly sealed channels through both connectors is created.

Returning again to FIG. 2, as part of a patient temperature control system, the male machine connector 13 may be further connectable to a hose assembly 14 employable for circulating medical fluid to and from the temperature patient temperature control pad. Included as part of the hose assembly 14 may be one or more intermediate connector devices which are employed to connect with hoses in fluid communication with the patient temperature control pad. The one or more intermediate connector devices may comprise at least one male intermediate connector 30 and at least one female intermediate connector 19 specially configured to engage with one another and further provide a plurality of sealed flow paths between the temperature control system and the temperature control pad for circulation of the medical fluid.

Figure 6A:
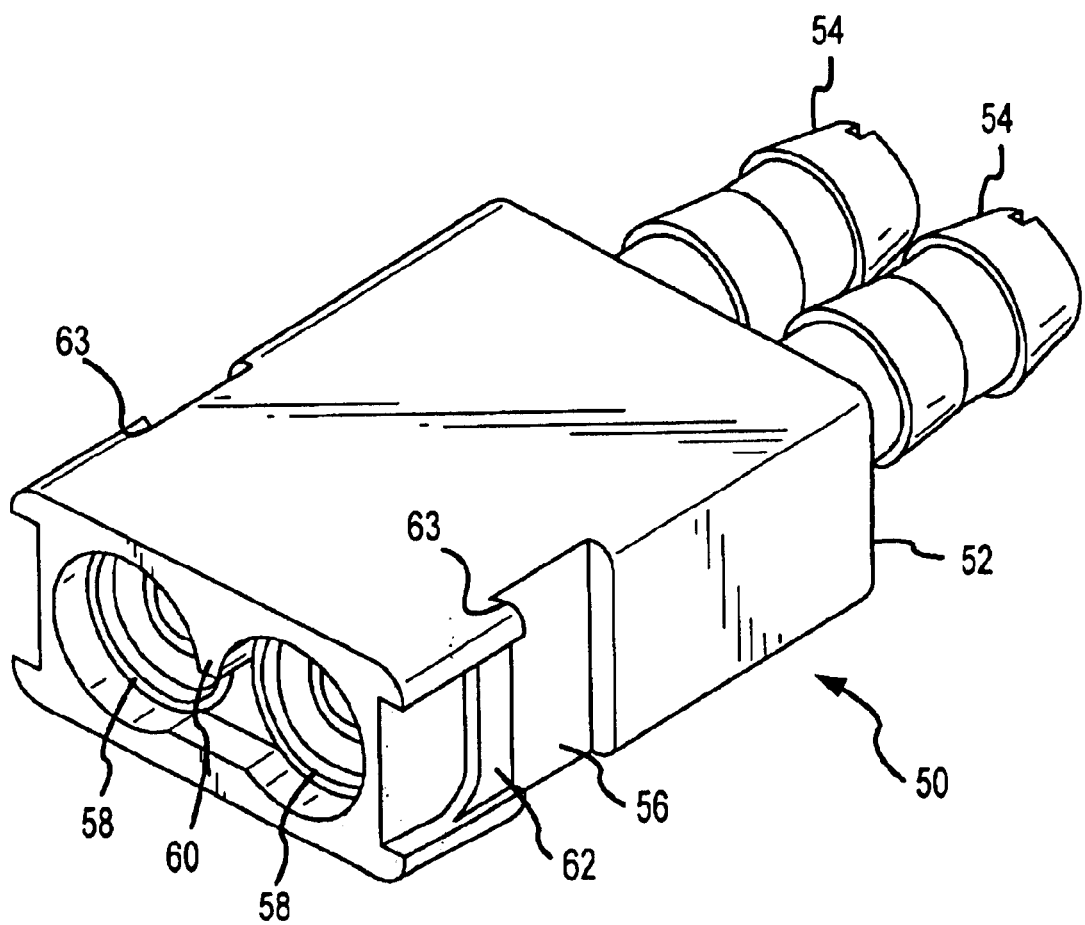
FIGS. 6a–c disclose views of one configuration of the female intermediate connector.

A geometric view of one configuration of a- female intermediate connector 50 is disclosed in FIG. 6a. Incorporated in the female intermediate connector 50 are hose ends 54 which are configured to compressibility fit within the attachment portion of a plurality hoses which may be further connectable, for example, to male machine connector 13. In an alternate configuration, which is shown in FIG. 2 and is to be described in greater detail below, the connection ends may be replaced the one-piece hose structure 15 with a plurality of flow channels formed therein. The one-piece hose structure 15 is further connectable to the male machine connector 13.

Figure 6B:
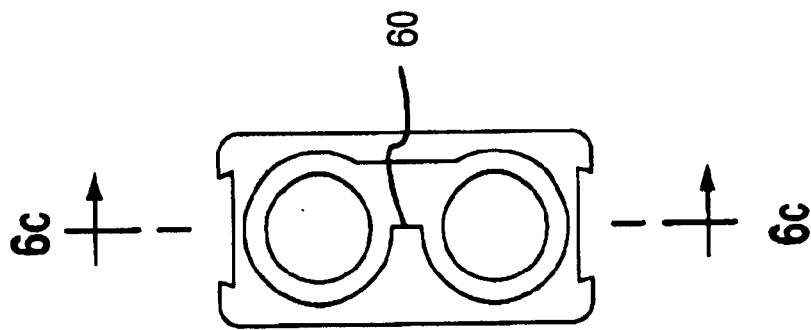
Figure 6C:
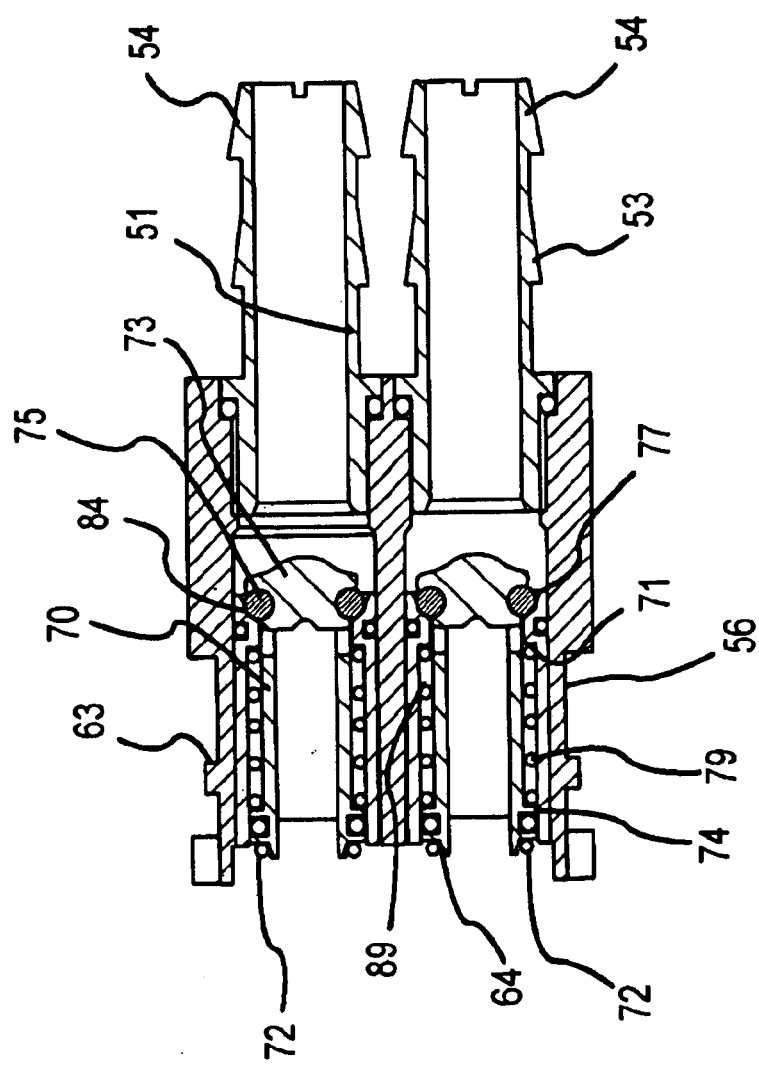

As seen in the cross sectional view of FIG. 6c, the female intermediate connector 50 further includes fluid channels 51 and 53 which extend from the hose ends 54 through body portion 52. The channels exit through receiving end 58. See FIG. 6a. Receiving end 58 is configured as a cavity in the body portion which is shaped to receive a portion of a male intermediate connector 30. Although the female intermediate connector 50 disclosed in FIGS. 6a–c is shown to include a single receiving end, other configurations of the female intermediate connector 50 may include a plurality of receiving ends, wherein one female intermediate connector 50 is connectable to a plurality of male intermediate connectors 30 simultaneously.

Continuing on with the female intermediate connector assembly 50, further included within the body portion 52 of the female intermediate connector is a moveable valve device which is manipulable to open and close upon insertion of the male connector. Returning again to the cross sectional view of FIG. 6c, the details of the valve device may be better viewed. A moveable valve device is positionable in each of the channels 51 and 53 for controlling the flow of medical fluid therethrough. Shown in particular, is a valve plunger 70 which has incorporated therein a number of openings 84, which depending on the position of the plunger in the channel, provide for fluid flow through the female intermediate connector 30. Surrounding the body portion of the valve plunger are springs 79, which are compressible against spring stop 71 when the male intermediate connector 30 is inserted. The insertion end 32 of the male intermediate connector 30 initiates movement of the plunger within the channels, such that the openings in the plunger are moved to a position which provides for circulation of the medical fluid.

Each plunger further includes an O-ring seal 72 which contacts an internal surface of the insertion end 32 of the male intermediate connector 30 when inserted. The plunger seal 74 is further employable to move with the plunger device and provide a fluid seal even while the plunger is moving or is moved. At the opposite end of the plunger device is a cap 73 which includes a valve seal 75 that provides for the sealing of the valve device upon removal of the male intermediate connector 30. The sealing occurs when the valve spring 20 decompresses and moves the plunger back towards the receiving end. At this point, the valve seal 75 contacts seat 84 and seals off any fluid flow therethrough.

Returning again to FIG. 6a, further incorporated into the body portion 52 are a number of engagement surfaces 63 configured for receiving and engaging an engagement arm portion of the male intermediate connector 30. As was will be described in greater detail below, the engagement surface 63 is configured as a lip which interlocks with a corresponding lip configured on an engagement arm of an insertable male connector.

Disclosed in the view provided in FIG. 6b, is a view of orientation device 60 incorporated into the body portion 52. This orientation device provides a non-symmetrical feature to the receiving end 58 of the female intermediate connector 50, which in turn provides for the insertion of the male intermediate connector 30 at only a particular orientation. The desirability of this feature will be described in greater detail below.

Figure 7A:
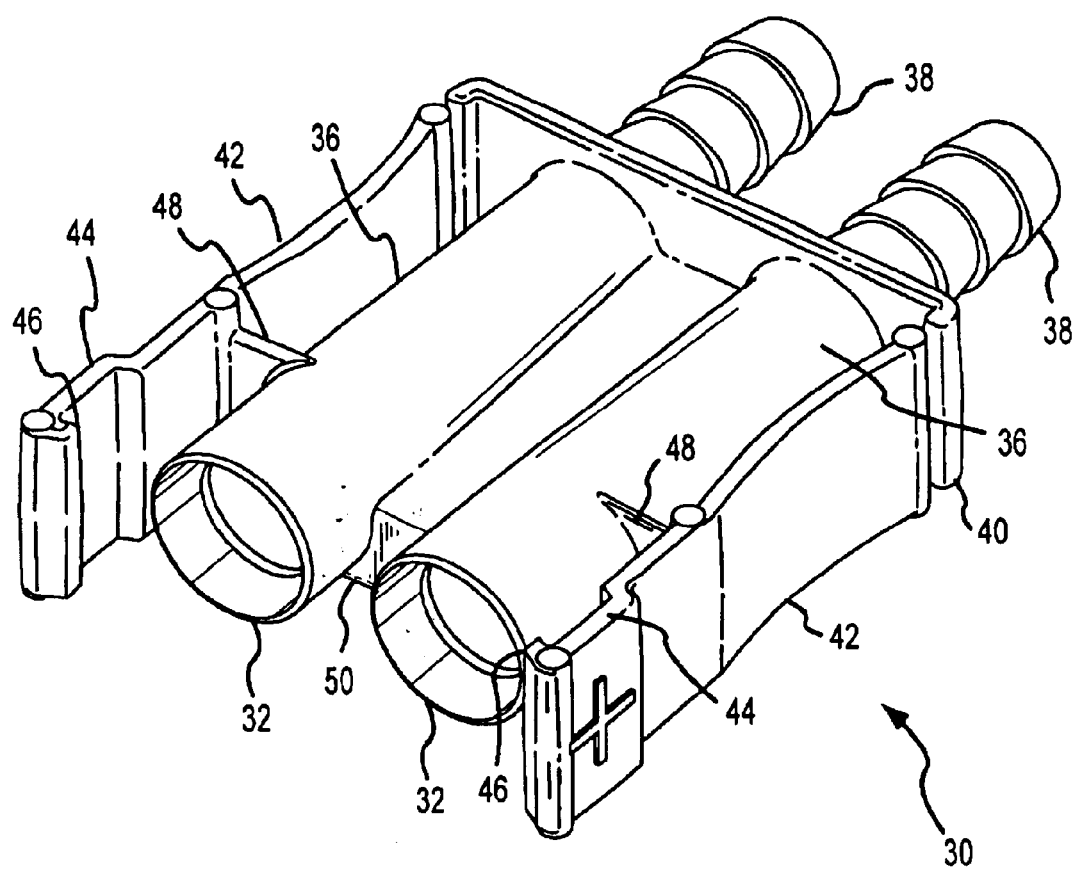
FIGS. 7a–c disclose views of the male intermediate connector.
Figure 7B:
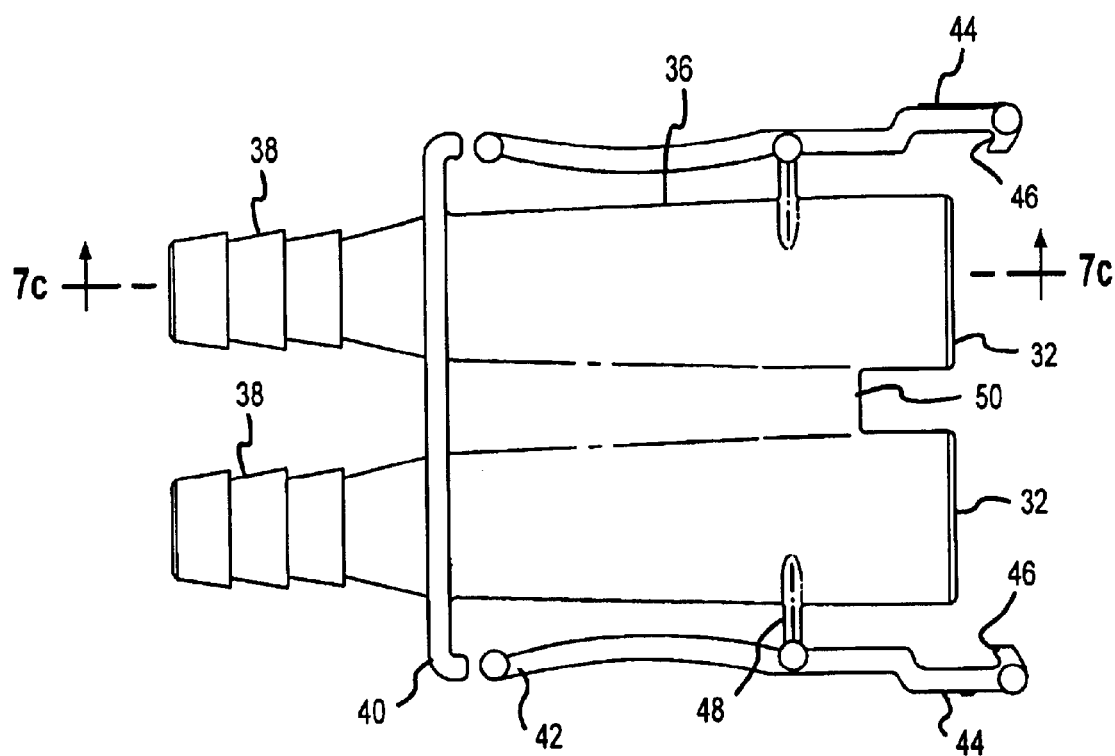
Figure 7C:
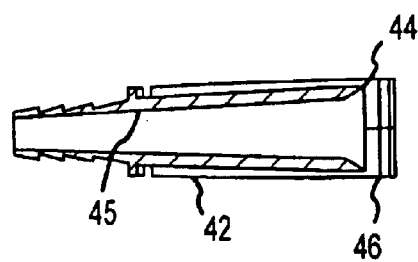

Views of one configuration of the male intermediate connector 30 configured to be interconnectable with the female intermediate connector 50 described above are provided in FIGS. 7*a*–*c*. Disclosed in FIG. 7*a* is a geometric view of the male intermediate connector 30. The male intermediate connector 30 includes a body portion 36 within which are formed fluid channels which pass from an insertion end 32 to a hose end 38. The hose end 38 is configured such that it is insertable within one end of a hose portion which in turn is interconnected and/or interconnectable to a patient temperature control pad or another connector. A removal/insertion arm 40 is configured to be employed in the insertion and removal of the male intermediate connector 30 with an female intermediate connector 50.

The insertion end 32 is configured to be insertable in a female intermediate connector 50. In particular,insertion end 32 may be configured to contact one or more sealing devices within a portion of the female intermediate connector 50 upon insertion so as to establish a fluid seal. During operation, depending on the direction of the flow, fluid will pass from insertion end 32 unobstructed to hose end 38 and vice versa. A cross sectional view of one of the fluid channels 45 through the male intermediate connector 50 is shown in detail in the view of FIG. 7*c*.

Also incorporated into the male intermediate connector 30 are one or more devices which provide for the engagement and proper alignment of the male intermediate connector 30 within a female intermediate connector 50. For engagement with the female intermediate connector 50, extending from the body portion 36 are one or more flex arms 48. The flex arms 48 may be constructed of a material which is the same or similar to the material use to form the body 36, wherein the flex arms 48 have sufficient flexibility to deform about the point of the attachment of the flex arm 48 to body 36. Further, attached to the flex arm 48 is latch arm 42 which is rotatable about an attachment point to flex arms 48 when a force is applied. When the force is removed, the elasticity of flex arm 48 returns the latch arm 42 to its original position.

Opposite the latch arm 42 portion is the attachment arm 44. Incorporated into the attachment arm 44 is an engagement lip 46 which is configured to interlock with a corresponding lip on an engagement surface 63 of a female intermediate connector 50. The attachment arm 44 and interlocking lip 46 of the male intermediate connector 30 are configured such that when a force is applied to the latch arm 42, which moves it closer to the body portion 36, the engagement arm 44 rotates away from the first end 32. When the force is released the elastic characteristics of the flex arm 48 returns the attachment arm with engagement lip 46 to its original position so that the engagement lip 46 may contact a corresponding engagement surface 63 on the female intermediate connector 50.

With regards to the alignment of the male and female intermediate connectors 50, further incorporated into the male intermediate connector 30 is orientation flange 33. Orientation flange 33 extends between the channels incorporated into body 36 and provides the functionality such that the male intermediate connector 30 may only be insertable in a female intermediate connector 50 at a particular orientation. In essence, this orientation device provides a non-symmetric feature to the insertable portion of male intermediate connector 30.

Figure 8B:
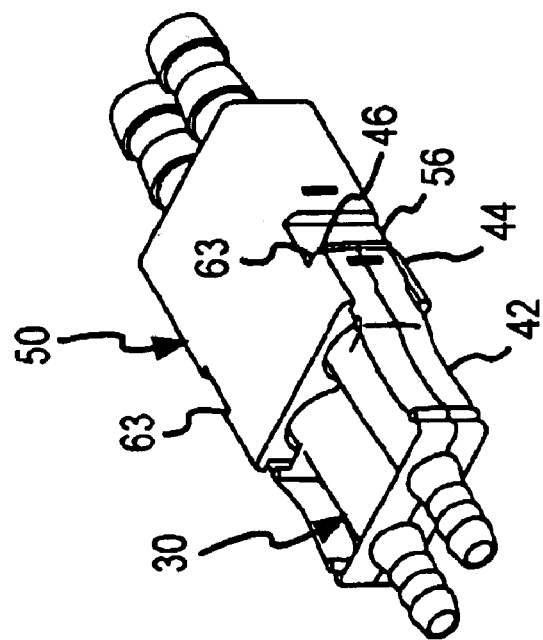
FIGS. 8a–f disclose views of the male and female intermediate connectors in operation.
Figure 8A:
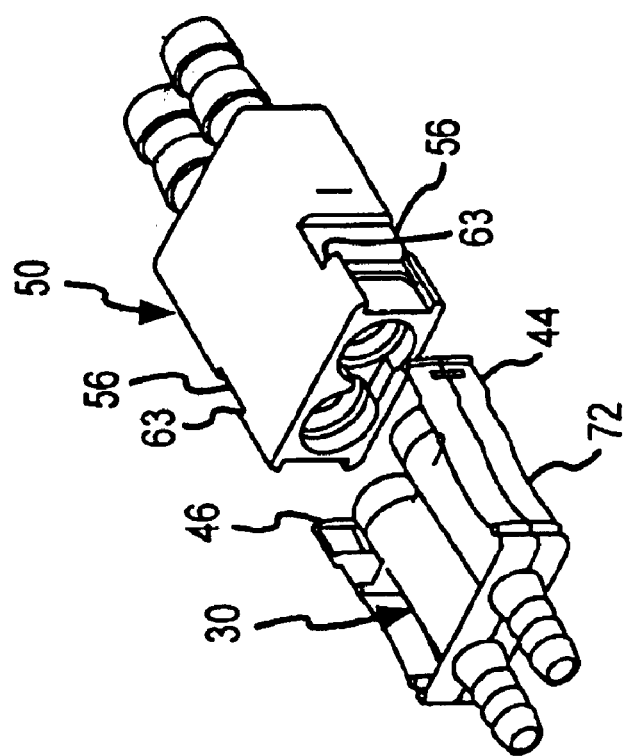
Figure 8C:
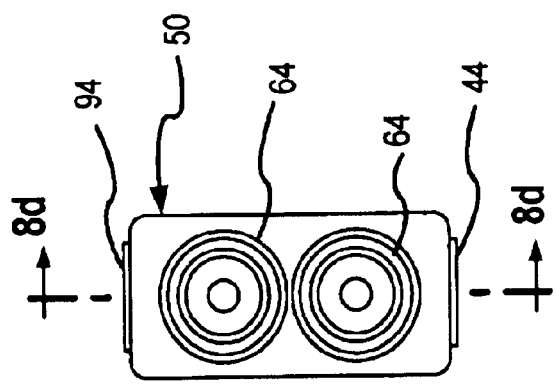

The engagement and disengagement of the male and female intermediate connectors may be better understood through study of FIGS. 8*a*–*d*. In particular, FIG. 8*b* shows the engagement of the male and female intermediate connectors, assemblies while FIG. 8*a* shows the connectors 30, 50 in a disengaged state. In order to initially engage the intermediate connectors the male and female intermediate connectors 30, 50 are first aligned. As part of the alignment process, the orientation flange 33 on the male intermediate connector 30 is positioned in a manner to as not to contact orientation device 60 upon insertion. More specifically, if the orientation device 60 contacts orientation flange 33 on the male intermediate connector 30, the male intermediate connector 30 is not insertable into the receiving end 58. Conversely, if the orientation device 60 is opposite the orientation flange 33 the male intermediate connector 30 is insertable in the receiving end 58 of the female intermediate connector 50 and a fluid tight connection may be made. The orientation devices provide the advantage that the wrong channels through the male and female intermediate connectors 30, 50 will not be fluidly connected, potentially affecting circulation of the medical fluid through the system.

Prior to insertion of the male intermediate connector 30 in the female intermediate connector 50, a force may be applied to attachment arms 42, preferably with one hand using, for example, the thumb and forefinger, which moves the attachment arms 42 towards the body portion 36 and the engagement arms 44 with interlocking lip 46 far enough away so as to clear the exterior body of the female intermediate connector 50.

The insertion end 32 of the male intermediate connector 30 may then be inserted within the receiving end 58 of the female intermediate connector 50 such that the interior surface of the insertion end 32 contacts the O-ring seal 72 on the valve plunger 70 which in turn pushes the plunger and compresses the valve spring. The plunger is moved to the point that the openings in the plunger body allow for fluid flow through the female intermediate connector 50.

Figure 8D:
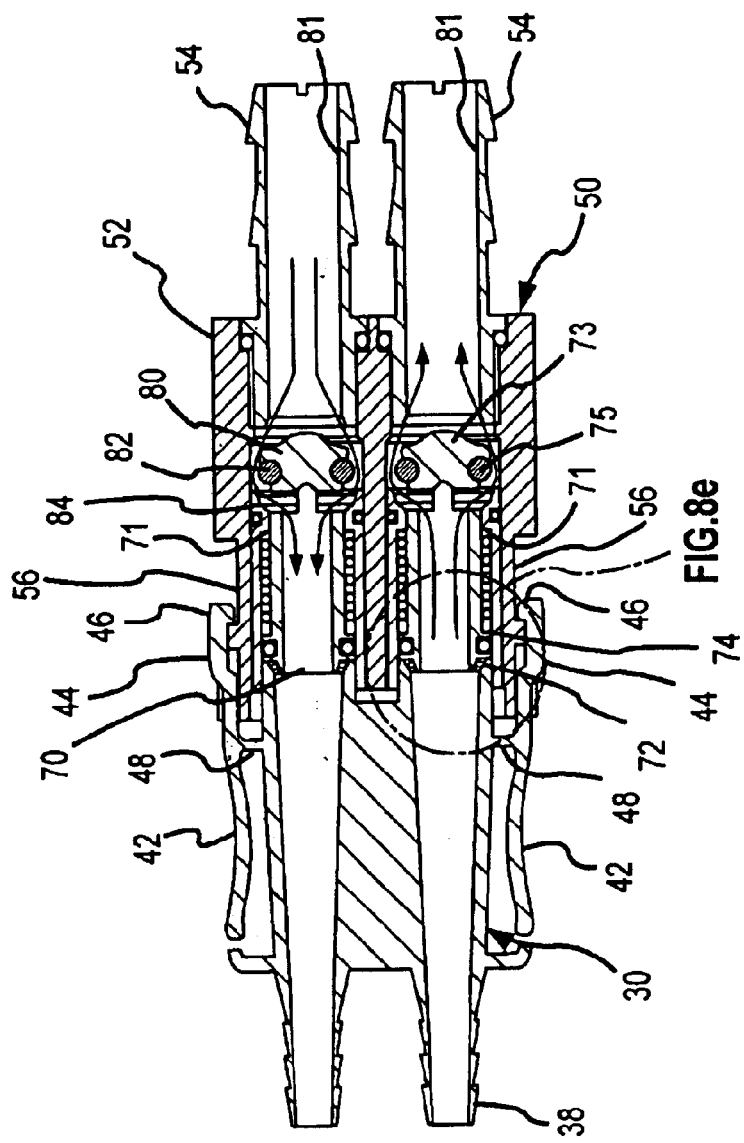

An example of an open valve within the female intermediate connector 50 is shown in the cross sectional view provided in FIG. 8*d*. As can be seen, when the male intermediate connector 30 is inserted, the valve spring 79 is compressed and head 80, with seal 82, is moved clear of valve seat 84 thus providing a fluid through the connector. As can be seen, in a circulating system such as the one described herein, the fluid may flow in different directions in the different channels.

Figure 8F:
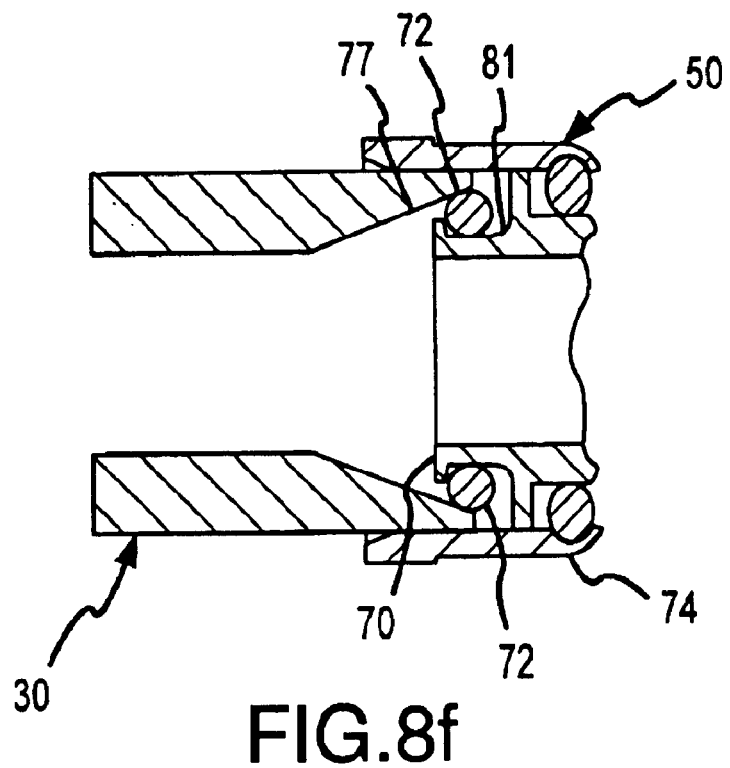
Figure 8E:
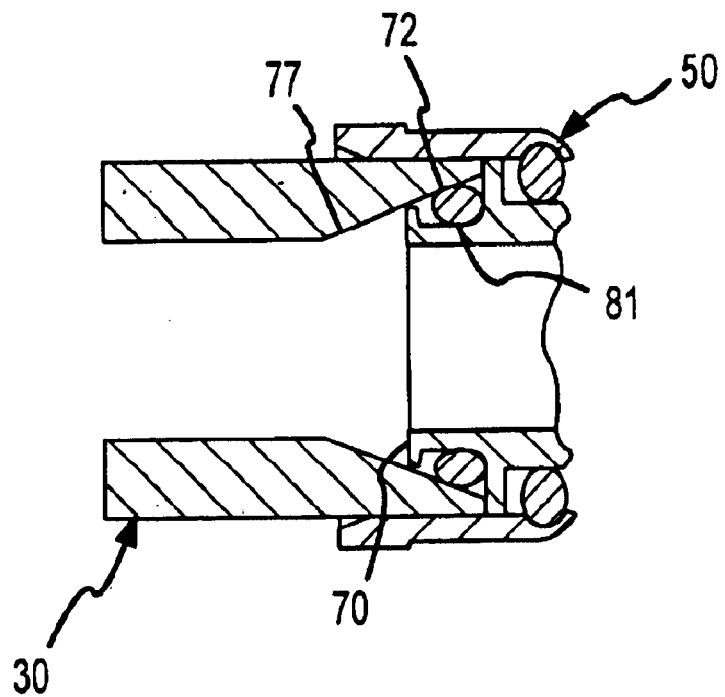

The fluid tight seal created between the male and female intermediate connectors 30, 50 upon connection may be better understood through the sectional views provided in FIGS. 8*e* and *f*. Disclosed in the view of FIG. 8*e* is a cross sectional view of the male intermediate connector 30 and female intermediate connector 50 in contact just prior to establishing the fluid tight seal. As can be seen, the male intermediate connector 30 includes an internal, tapered surface 77 which contacts an O ring 72 mounted on the valve plunger 70. The valve plunger 70 has an external tapered surface 81 that contacts the opposite side of the O-ring.

As the male intermediate connector 30 is pushed into the female intermediate connector 50, the O-ring 72 rolls between the two tapered surfaces 77 and 81. During the insertion, the Owing rolls rather than slides against the mating surfaces so that wear of the O-ring is minimized. Further, rolling rather than sliding also reduces the force required to engage the two connectors. Since the two surfaces in contact with the O-ring are tapered, the O-ring is compressed as the male intermediate connector 30 is moved along the axis of the flow channel for the female intermediate connector 50.

Shown in FIG. 8*f* is a view of the male and female intermediate connectors 30, 50 fully engaged. As is seen, because the internal tapered surface 77 of the male intermediate connector has a larger taper angle than the external surface of the valve plunger, thus the O-ring is squeezed into a wedge shape. The O-ring gland area is tapered so that an increased vacuum inside the connectors pulls the O-ring into a smaller section of the gland. This increases the compression in the O-ring, which in turn increases the contact stress between the O-ring and tapered surfaces. The result is that increased vacuum improves the seal by tightening the O-ring in the gland.

The fluid tight seal described above is maintained by the mechanic engagement of the male and female intermediate connectors 30, 50. The mechanical engagement of the male and female intermediate connectors 30, 50 may be better understood through further study of FIG. 8d. Once the engagement portion 46 of attachment arm 44 passes within the engagement area 56 on the exterior of the female intermediate connector 50, the latch arm of the male intermediate connector 30 may be released, which in turn rotates the engagement lip 46 such that it contacts engagement area 56. Releasing the male intermediate connector 30 has the further effect that the compressed valve springs begin to uncompress, thus moving the engagement lip 46 into engagement surface 63, thus interlocking the two surfaces. The compressive force applied by the valve springs keeps the two surfaces in contact, and the diagonal direction, relatively, of the surfaces resists lateral movement of the engagement arm with respect to the female connector body thus maintaining engagement between the male and female connectors.

In order to disengage the male intermediate connector 30 from the female intermediate connector 50, an insertion force is applied to the male intermediate connector 30, further moving the valve plunger 70 and further compressing the valve spring. The further movement of the male intermediate connector 30 acts to move the engagement devices and engagement surfaces clear of each other. Forces are then applied simultaneously (using the thumb and forefinger, for example) to all of the latch arms 42 to move them towards the body 36 of the male intermediate connector 30. The application of these forces acts to move the engagement arms 44 away from the body portion 52 of the female intermediate connector 50, whereby maintaining the force on the latch arms 42 the insertion force may be reversed and the male intermediate connector 30 removed. It should be noted that in the configuration of the invention described herein, simultaneous application of force to all latch arms 42 is necessary to perform the removal of the male intermediate connector 30. If one the engagement arms is not moved, the interlocking lip 46 on the arm is not moved and will contact the corresponding interlocking lip 46 on the engagement surface, thus interfering with removal of the male intermediate connector 30. The necessity of this simultaneous movement is a safety feature which acts to avoid inadvertent disconnections of the male and female intermediate connectors 30, 50.

As was discussed above, the male machine connector 13 may be included as part of a connector assembly This connector assembly may include a male machine connector 13, an intermediate one-piece hose 15, as well as a female intermediate connector 50. In one configuration of the invention the connector assembly may be a unitary piece, in that it may be made up of a number of different pieces, and manufactured in manner such that it cannot be disassembled without damaging its function. Disclosed in FIGS. 9a–f are various views of this connector assembly.

Figure 9A:
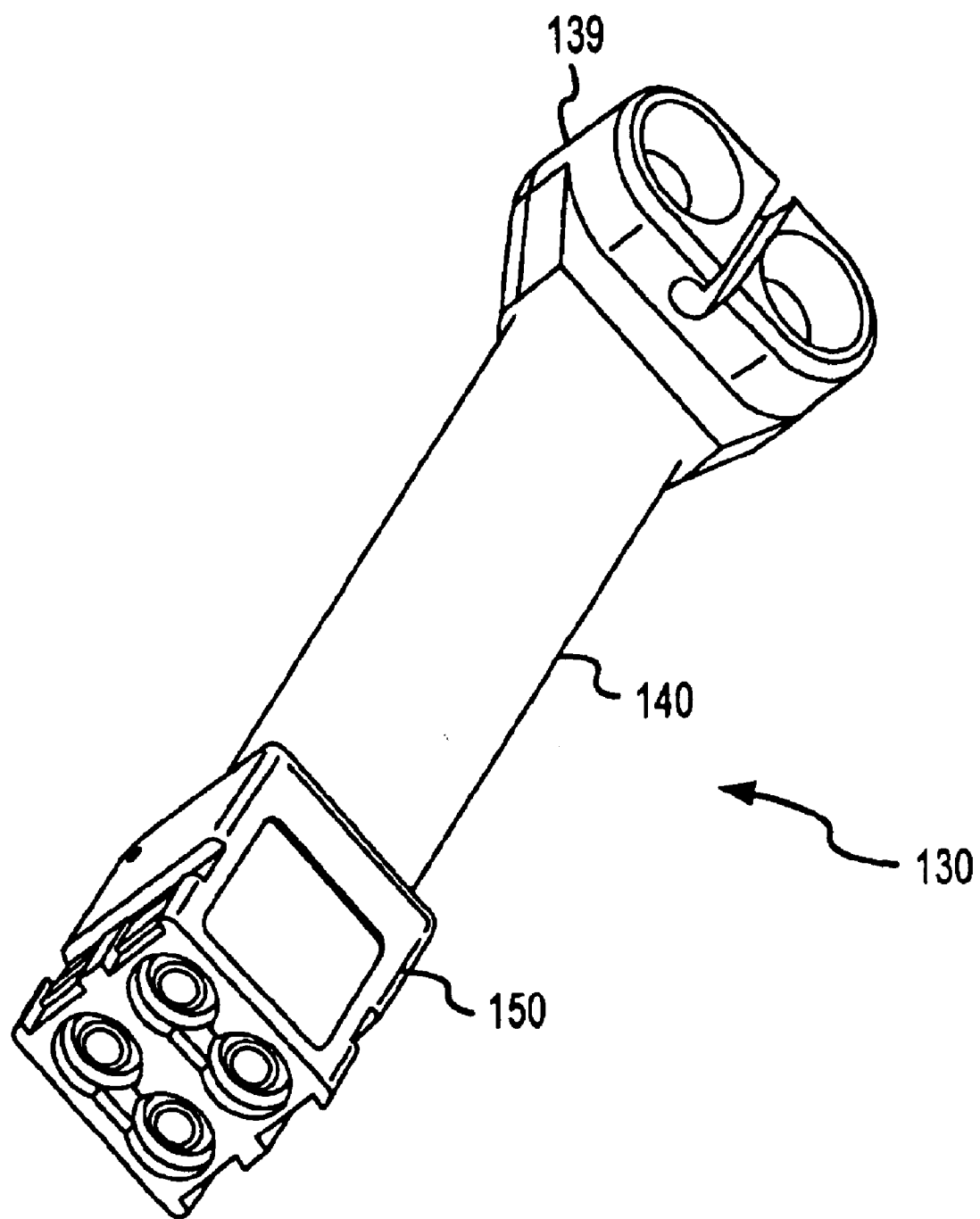

Disclosed in FIG. 9a is a geometric view of the connector including a male machine connector 13 connected to the one-piece hose section 140, which in turn is connected to female intermediate connector assembly 150. As seen in FIG. 9b and the cross sectional view of FIG. 9e, incorporated into the hose section 140 are fluid channels 140 and 142. The channels are in communications with channels through the male machine connector 13 and the female intermediate connector 50 assembly portions. Hose section 140 maybe formed out of any number of hard plastic, rubber, or composite materials of sufficient stiffness.

In the configuration shown in FIG. 9a, the female machine connector assembly is configured to interconnect with a maximum of two male intermediate connector assemblies. As seen in FIG. 9d, configured into the bottom of female connector assembly 150 are two receiving ends 171 and 173, where each end includes openings 170 and 172 to the fluid channels incorporated therein. As seen in the cross sectional view, each of the channels includes a valve assembly which operates in the same manner as described above for the female intermediate connector 50. For the channels which circulate fluid in the same direction, such as those shown in the cross sectional view of FIG. 9e, they are further in communication with a common manifold 166 which is further in communications with a channel, channel 142 in this view, of the hose section 140. It is further seen that each receiving end 171 and 173 includes a set of engagement surfaces 152 configured for engaging and interlocking with the engagement devices incorporated in the male connectors.

Figure 10:
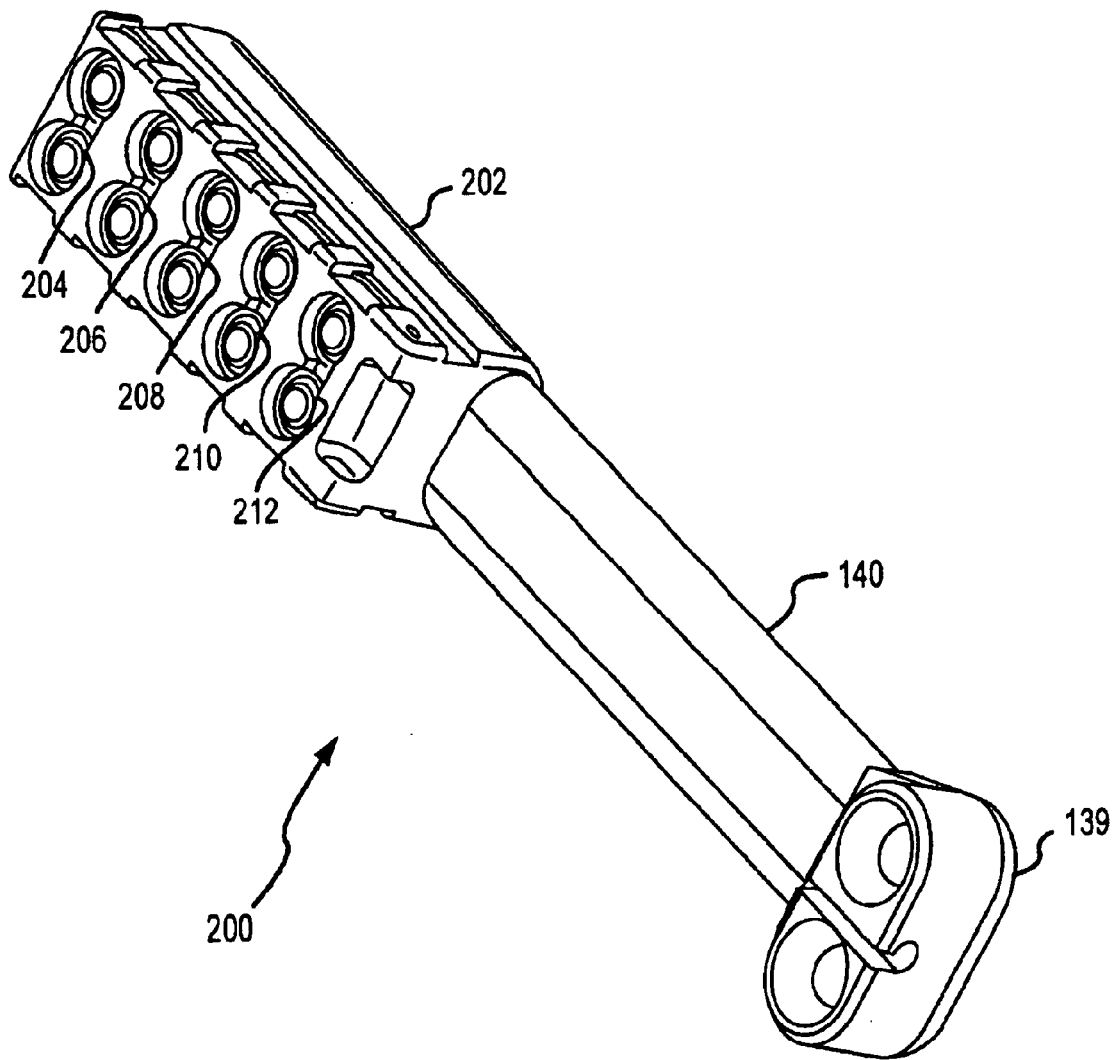
FIG. 10 discloses a geometric view of another configuration of the machine male connector assembly.

Yet another configuration of the male machine connector assembly is disclosed in FIG. 10. In this configuration the connector assembly 200 includes a female connector portion 202 with receiving ends 204–212 for interconnecting with a maximum 5 intermediate male connectors simultaneously. The configurations of the male machine connector assembly, especially the intermediate female connector, are exemplary, and one skilled in the art would know that the female intermediate connector portion can be configured with any number of receiving ends so as to connect with any number of male intermediate connectors. In this configuration it further seen that receiving ends may be incorporated in any number of surfaces of the intermediate female connector so as to facilitate the ergonomic design of the overall system.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A connector for use in a patient temperature control system which includes a medical fluid processing apparatus for processing medical fluid, comprising:
 a body portion which includes a plurality of fluid channels formed therein, wherein the body portion is one of interconnected and interconnectable to at least one of:
 the medical fluid processing apparatus and a patient temperature control pad through which a fluid may be circulated;

an interconnection end configured to interconnect with at least one other connector employable in the patient temperature control system, where the interconnection end further includes at least one orientation device configured to provide for the interconnection of the connector and the at least one other connector at an orientation which provides for circulation of the fluid through the system in a predetermined direction; and a rotatable engagement device extending through a portion of the interconnection end, the rotatable engagement device being configured to pass within a portion of the other connector, wherein the connectors are engaged at a first rotational position of the rotatable engagement device and disengaged at a second rotational position of the rotatable engagement device.

2. The connector apparatus of claim 1 wherein the connector is configured as a female connector and the interconnection end is configured as a receiving end, wherein the receiving end further includes the rotatable engagement device extending through a portion of the receiving end, the rotatable engagement device being configured to pass within a portion of a male connector end and upon rotation of the rotatable engagement device mechanically engage and hold the male connector, and upon further rotation, disengage from the male connector.

3. The connector of claim 2 wherein the receiving end comprises a wall structure which encircles a cavity within which the openings and the fluid pathways are locatable, wherein the rotatable engagement device includes at least one shaft like member which extends through opposing walls of the wall structure.

4. The connector of claim 3 wherein the shaft like member is further connected to a manipulation arm locatable outside the cavity, the manipulation being employable for rotating the shaft like member to a desired rotational orientation.

5. The apparatus of claim 3 wherein the cavity is further configured to include an interior cross sectional shape substantially similar to an exterior cross sectional shape of the male connector and the rotational engagement device positioned so as to provide for insertion of the male connector in the receiving end only at the predetermined orientation.

6. The connector of claim 3 wherein the at least one shaft like member includes a semi-circle cross section.

7. A male machine connector assembly for use in a patient temperature control system, comprising:

a body portion with a plurality of fluid channels formed therethrough;

an insertion end configured in the body portion, the insertion end including openings to the fluid channels and is further configured to fluidly seal with a female connector end upon insertion so as to establish a plurality of sealed fluid paths through the male and female connectors; and at least one engagement portion integrated in the male connector which is configured to receive a rotatable engagement device and is further configured such that upon rotation of the device the male and female connectors are mechanically engaged.

8. The assembly of claim 7 wherein the engagement portion comprises a slot configured in the insertion end, wherein the slot allows a portion of the rotatable engagement device to pass within the slot at a first rotational orientation and to engage and hold the portion of the rotatable engagement device at a second rotational orientation.

9. The assembly of claim 7 wherein the engagement portion is positioned such that the insertion end is insertable in the female connector only at predetermined orientation.

10. The assembly of claim 8 wherein the of the rotatable engagement device is a shaft like member configured with a semi-circle cross section and the slot includes a cylindrical section and a straight section wherein the shaft like member passes through the straight section into the cylindrical section at a first orientation and is rotatable to a second orientation to engage the cylindrical section.

11. The assembly of claim 9 further comprising a one piece hose section with a plurality of fluid passageways formed therethrough, the hose section being connectable to the male connector at an end opposite the insertion end.

12. The assembly of claim 11 further including an intermediate connector device connectable to the hose section at an end opposite the connection to the body portion.

13. The assembly of claim 12 wherein the intermediate connector device comprises an intermediate female connector device configured to interconnect with one or more hose assemblies which include a male connector.

14. The assembly of claim 13 wherein the one or more hose assemblies provide fluid circulation to at least one patient temperature control pad.

15. A male intermediate connector apparatus for use in a patient temperature control system, comprising:

a body portion configured to include a plurality of fluid channels formed therethrough, the body portion further including an insertion end with openings to the fluid channels, wherein the insertion end is configured to be insertable in a female connector so as to engage a portion of the female connector and provide a fluidly sealed flow path for each of the channels with the female connector;

said body portion further including an exterior orientation portion configured such that the male and female connectors are connectable at a predetermined orientation; and an engagement device including an arm interconnected to the body portion, the arm being manipulable to engage and disengage an engagement surface of the female connector when the insertion end is inserted in a receiving portion of the female connector.

16. The apparatus of claim 15 wherein the engagement device is configured to engage and disengage the engagement surface of the female connector through single handed manipulation.

17. The apparatus of claim 15 wherein the arm further comprises:

at least one flex arm extending substantially perpendicular from the body portion;

a latch arm positionable at an end of the at least one flex arm away from the body substantially perpendicular to the latch arm, wherein the latch arm includes a depressible portion configured on a first end and an engagement portion configured on a second end opposite the first end; and the flex arm being connectable to the latch arm in a manner such that application of a force to the first end rotates the second end and flex arm about the point of attachment of the flex arm and the body, and removal of the force returns the flex arm and latch arm to an original position.

18. The apparatus of claim 17 wherein the engagement portion is configured as at least one interlocking lip, such that when the engagement portion engages a matching interlocking surface on the female connector, the engaged structure resists lateral movement.

19. The apparatus of claim 15 wherein the body portion in configured to includes a cross sectional shape through a plane substantially perpendicular to one or more of the centerlines of the fluid channels which is includes a non-symmetric feature.

20. The apparatus of claim 15 wherein the body portion further includes an alignment flange positionable between the channels which provide for the engagement of the male and female connectors at the predetermined orientation.

21. The apparatus of claim 15 further configured to be at least one of: interconnected and interconnectable to at least one temperature control pad positionable on patient for providing temperature control.

22. The apparatus of claim 15 further comprising at least one internal tapered surface configured to roll and compress an O-ring encircling an external surface of the female connector upon interconnection of the male and female connector.

23. A female intermediate connector assembly for use in a patient temperature control system, comprising:
 a body portion configured with a plurality of fluid channels formed therethrough, the channels passing from at least one receiving end to an attachment end;
 said at least one receiving end configured to receive and fluidly seal with a male connector and provide a fluidly sealed flow path for each of the channels within the female connector upon insertion of said male connector in said receiving end;
 said at least one receiving end being further configured to receive the male connector only at a predetermined orientation; and
 at least one engagement surface configured to receive an engagement portion of an attachment arm interconnected to the male connector upon insertion of a portion of the male connector in the receiving end.

24. The assembly of claim 23 wherein the engagement surface is configured as at least one ledge incorporated into the body portion which is sized to receive the engagement portion of the attachment arm.

25. The assembly of claim 23 further including at least one valve device positionable within each of the fluid channels which are configured to seal with the male connector assembly upon insertion in the receiving end and establish a flow path therethrough, the valve device being further configured to seal the receiving end upon removable of the male connector assembly from the receiving end.

26. The assembly of claim 25 wherein the at least one valve device comprises a movable plunger in communication with at least one compressible spring, wherein upon insertion of the male connector in the receiving end the plunger is moved and the spring is compressed thereby opening the passageway for fluid flow, and upon removal of the male connector the compressible spring moves the plunger back to its original position thereby fluidly sealing the passageway.

27. The assembly of claim 25 wherein the engagement surface is configured as an interlocking lip which interlocks with a matching lip on an attachment arm of a male connector, wherein pressure exerted by the compressible spring limits lateral movement of the interlocked surfaces so as to maintain engagement.

28. The assembly of claim 23 wherein the receiving end is further configured to include a cavity with an interior cross sectional shape substantially equal to an exterior cross sectional shape of the male connector so as to provide for insertion of the male connector in the receiving end at the predetermined orientation.

29. The assembly of claim 28 wherein the interior cross sectional shape includes at least one substantially nonsymmetrical feature which provides for insertion of the male connector at the predetermined orientation.

30. The assembly of claim 23 wherein the body portion is further configured to include a plurality of the receiving ends so as to be configured to engage and disengage with a plurality of the male connectors.

31. The assembly of claim 30 wherein each of the plurality of receiving ends is configured with at least one of the engagement surfaces for receiving and interlocking with an engagement device of the at least one male connector.

32. The assembly of claim 23 wherein the attachment end is employed to attach to a one piece hose apparatus with a plurality of fluid channels formed therethrough, wherein the hose apparatus is further attached to a connector device connectable to this temperature control system.

33. The assembly of claim 23 wherein the male connector is at least one of interconnected and interconnectable connectable to at least one patient temperature control pad.

34. The assembly of claim 23 further comprising an O-ring encircling at least one external tapered surface within the receiving, wherein the O-ring is rollable and compressible between a tapered internal surface of the male connector and the external tapered surface to create a fluid tight seal with the male connector.

35. A female connector assembly for use in a patient temperature control system, comprising:
 a body portion having an inlet fluid channel and an outlet fluid channel passing therethrough between an attachment end and a plurality of receiving ends;
 said attachment end having a single inlet and a single outlet in fluid communication with said inlet channel and said outlet channel, respectively, said attachment end being one of: interconnected and interconnectable to a medical fluid temperature circulating apparatus; and
 said plurality of receiving ends each having a single inlet and a single outlet in fluid communication with said inlet fluid channel and said outlet fluid channel, respectively, and each said receiving end being configured to receive and engage an insertion end of a male connector so as to create first and second sealed fluid paths with the male connector when so engaged.

36. The assembly of claim 35 wherein said male connector is interconnected to a patient temperature control pad such that said inlet fluid channel and outlet fluid channel provide for the circulation of fluid from said medical fluid temperature circulating apparatus through said pad when said male and female connectors are engaged.

37. The assembly of claim 35 further including at least one valve device positionable within each of the receiving ends which are configured to seal with the male connector upon insertion in the receiving end and establish a flow path therethrough, the valve device being further configured to seal the receiving end upon removable of the male connector from the receiving end.

38. The assembly of claim 37 wherein the at least one valve device comprises a movable plunger in communication with at least one compressible spring, wherein upon insertion of the male connector in the receiving end the plunger is moved and the spring is compressed thereby opening the passageway for fluid flow, and upon removal of the male connector the compressible spring moves the plunger back to its original position thereby fluidly sealing the passageway.

39. The assembly of claim 35 wherein each of the plurality of receiving ends is further configured to receive a male connector only at a predetermined orientation.

40. The assembly of claim 35 wherein each of the plurality of receiving ends is configured with at least one of the engagement surfaces for receiving and interlocking with an engagement device of a male connector.

* * * * *

UNITED STATES PATENT AND TRADEMARK OFFICE
CERTIFICATE OF CORRECTION

PATENT NO. : 6,802,855 B2
DATED : October 12, 2004
INVENTOR(S) : Ellingboe et al.

It is certified that error appears in the above-identified patent and that said Letters Patent is hereby corrected as shown below:

Column 9,
Line 16, delete "particular,insertion", and insert therefor -- particular, insertion --.

Signed and Sealed this

Eighteenth Day of October, 2005

JON W. DUDAS
*Director of the United States Patent and Trademark Office*